US006033850A

United States Patent [19]
Purvis

[11] Patent Number: 6,033,850
[45] Date of Patent: *Mar. 7, 2000

[54] ELECTROCHEMICAL DENATURATION OF DOUBLE-STRANDED NUCLEIC ACID

[75] Inventor: Duncan E. Purvis, Hartford, United Kingdom

[73] Assignee: Affymetrix, Inc., Santa Clara, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/704,657

[22] PCT Filed: Mar. 14, 1995

[86] PCT No.: PCT/GB95/00542

§ 371 Date: Sep. 13, 1996

§ 102(e) Date: Sep. 13, 1996

[87] PCT Pub. No.: WO95/25177

PCT Pub. Date: Sep. 21, 1995

[30] Foreign Application Priority Data

Mar. 15, 1994 [GB] United Kingdom ............... 9405016
Feb. 6, 1995 [GB] United Kingdom ............... 9502284

[51] Int. Cl.[7] ............... C12Q 1/68; C12P 19/34
[52] U.S. Cl. ............... 435/6; 435/91.1
[58] Field of Search ............... 435/6, 91.1, 91.2, 435/91.5; 536/24.33; 935/77, 78; 204/196, 403

[56] References Cited

U.S. PATENT DOCUMENTS

| 4,945,045 | 7/1990 | Forrest | 435/25 |
| 5,527,670 | 6/1996 | Stanley | 435/6 |
| 5,607,832 | 3/1997 | Stanley et al. | 435/6 |
| B1 4,683,202 | 11/1990 | Mullis | 435/91 |

FOREIGN PATENT DOCUMENTS

| 201 184 | 12/1986 | European Pat. Off. . |
| 302 308 | 6/1989 | European Pat. Off. . |
| 92 04470 | 3/1992 | WIPO . |
| 93 15224 | 8/1993 | WIPO . |
| 93/15224 | 8/1993 | WIPO . |

OTHER PUBLICATIONS

Cassidy et al. Analyst 118:415–418, Apr. 1993.
Pawlowski et al, Some Aspects of the Copper(II)–DNA Interaction, Acta Biochimica Polonica, vol. 36 1989 No. 1.
Stanley et al., Amperometric enzyme–amplified immunoassays, J. of Immunological Methods 112 (1988) 153–161.
Brabec, Interaction of Nucleic Acids with Electrically Charged Surfaces, Biophysical Chemistry 9 (1979) 289–297.
Brabec et al., Raman Scattering from Nucleic Acids Adsorbed at a Silver Electrode, Biophysical Chemistry 23 (1985) 63–70.
Brabec, The Effects of Base Composition . . . of the Adsorbent, Bioelectrochemistry and Bioenergetics, 11 (1983) 245–255.
Valenta et al., The Electrochemical . . . Charged Interfaces, Biophys. Struct. Mechanism 1, 17–26 (1974).
Brabec et al., Interactions of Nucleic . . . Charged Surfaces, J. Electroanal. Chem. 88 (1978) 373–385.
Palecek, Adsorptive transfer stripping . . . the mercury surface, Bioelectrochemistry and Bioenergetics, 28 (1992) 71–83.
Palecek, New trends in electrochemical analysis of nucleic acids, Bioelectrochemistry and Bioenergetics, 20 (1988) 179–194.
Palecek, Adsorptive Transfer Stripping . . . at the Electrode Surface, Analytical Biochemistry 170, 421–431 (1988).
Brabec, Nucleic Acid Analysis by Voltammetry at Carbon Electrodes, Bioelectrochemistry and Bioenergetics, 8 (1981) 437–449.
Fultz et al., Mediator Compounds . . . A Compilation, Organic Analytical Research Div., Nat. Bur. of Standards, Mar. 1982.
Berg, Polarographic Possibilities in Protein and Nucleic Acid Research, Academy of Sciences of GDR.
Palecek, Modern Polarographic (Voltammetric) . . . Molecular Biology, Topics in Bioelectrochemistry and Bioenergetics, vol. 5, 1983.
Jelen et al., Chemically Reversible . . . Chain, Biophysical Chemistry 24 (1986) 285–290.
Nurnberg, Applications of Advanced . . . Bioelectrochemistry, Institute of Appl. Phys. Chem. Chem. Dept., Nucl. Res. Cntr. Juelich, Germany.
Palecek, Electrochemical Behaviour of Biological Macromolecules, Bioelectrochemistry and Bioenergetics, vol. 211 (1986).
Brabec et al., Interaction of Nucleic . . . Polynucleotides, Biophysical Chemistry 4 (1976) 79–92.
Eddowes et al., Novel Method . . . Cytochrome c, J.C.S. Chem. Comm. 1977, pp. 771–772.
Boublikova et al., Adsorptive Stripping Voltammetry of DNA, Studia Biophysica, vol. 114 (1986), No. 1–3, p. 83–90.
Palecek et al., Cyclic Voltammetry . . . Stripping Voltammetry, Analytica Chimica Acta, 187 (1986) 99–107.
Palecek et al., Absence of Unwinding . . . Neutral pH, Collection Czechoslov. Chem. Commun. vol. 44 (1979).
Palecek et al., Electrochemical analysis . . . d(CCAGC-CTGG), Bioelectrochemistry and Bioenergetics 23 (1990) 285–299.
Jelen et al., Nucleotide Sequence–Dependent . . . Charged Surface, Gen. Physiol. Biophys. (1985). 4. 219–237.
J.Immunot. Methods, vol. 112, No. 2, 1988 Elsevier, Amsterdam, NL, pp. 153–161, C.J. Stanley et al. "Amperometric enzyme–amplified immunoassays".

*Primary Examiner*—Eggerton A. Campbell
*Attorney, Agent, or Firm*—Margaret A. Powers; Townsend & Townsend & Crew

[57] ABSTRACT

Double stranded nucleic acid is denatured by subjecting a solution thereof to a voltage applied between electrodes spaced by no more than 1.5 mm in a time not previously achievable in electrochemical denaturation. PCR is practiced isothermally by periodic application of voltage to produce denaturation. Electrochemical cells and kits for use in the process are provided.

23 Claims, 1 Drawing Sheet

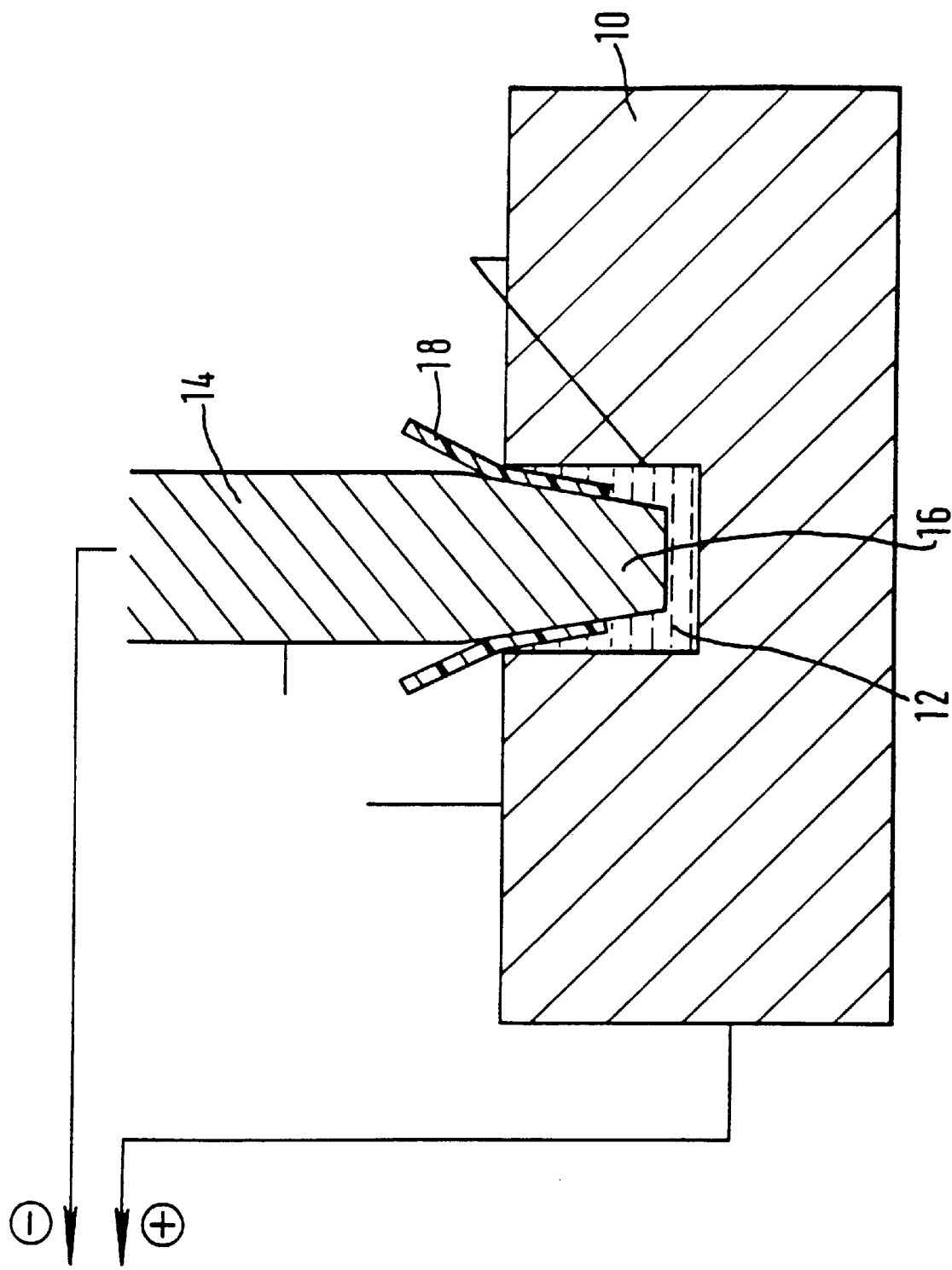

ELECTROCHEMICAL DENATURATION OF DOUBLE-STRANDED NUCLEIC ACID

This application claims benefit of international application PCT/GB95/00542, filed Mar. 14, 1995.

This invention relates to processes for the treatment of nucleic acid material in order to effect a complete or partial change from double-stranded form to single-stranded form and to processes of amplifying or detecting nucleic acids involving such denaturation processes.

Double-stranded DNA (deoxyribonucleic acid) and DNA/RNA (ribonucleic acid) and RNA/RNA complexes in the familiar double helical configuration are stable molecules that, in vitro, require aggressive conditions to separate the complementary strands of the nucleic acid. Known methods that are commonly employed for strand separation require the use of high temperatures of at least 60° C. and often 100° C. for extended periods of ten minutes or more or use an alkaline pH of 11 or higher. Other methods include the use of helicase enzymes such as Rep protein of E.coli that can catalyse the unwinding of the DNA in an unknown way, or binding proteins such as 32-protein of E.coli phage T4 that act to stabilise the single-stranded form of DNA. The denatured single stranded DNA produced by the known processes of heat or alkali treatment is used commonly for hybridisation studies or is subjected to amplification cycles.

Such separation is a prerequisite of a number of protocols involving the in vitro manipulation of nucleic acids, one example of which is a reaction that produces multiple copies of target sequences of DNA and which employs a heat-stable polymerase enzyme (U.S. Pat. No. 4,683,202, K. B. Mullis et al). This development, known as the polymerase chain reaction (PCR), is of significant commercial importance and strand separation is normally effected by heating the sample to approximately 95° C. The removal of the need to heat the sample would provide a number of benefits. For example, it allows the design of compact and readily controllable apparatus, and the use of higher fidelity mesophilic enzymes.

WO 92/04470 discloses a process whereby nucleic acid strands are separated by the application of an electric field. The advantages of the electrical method are discussed in greater detail, along with the method's application in amplification reactions such as PCR and ligase chain reaction. Forms of electrochemical cells for carrying out the reaction are described and also the use of "promoter" compounds that enhance the efficiency of denaturation.

Prior to WO92/04470, a number of other workers had described denaturation of DNA in electrochemical cells. However, in none of these cases was single-stranded product left free in solution in useful quantities. Rather, DNA appears to have become irreversibly bound to the surface of the electrode, in which condition it is not available for further participation in processes such as PCR. In the method of electrical denaturation described in WO92/04470, single strands accumulate in solution and their utility and integrity is confirmed by subsequently performing PCR.

In WO92/04470 electrical denaturation of DNA was carried out using an electrode comprising a central rod of glassy carbon encased in a teflon sleeve except at its end. The working electrode was of platinum mesh lying against the teflon sleeve. A calomel reference electrode was used, situated in a side chamber which was connected to the main cell by a capillary tube (see Stanley C. J. et al, J. Immunol. Meth. [1988], 112, 153–161). Using this apparatus the most rapid denaturation was achieved in 15 minutes with the working electrode at a potential of −1V with respect to the reference. The presence of NaCl in the reaction delayed denaturation.

In WO92/04470, a PCR reaction is conducted in which there are repeated denaturation operations conducted using the electrochemical cell described with intervening amplification stages. The denaturation stages are each conducted for a period of five minutes or longer and the total time for the PCR reaction is therefore very extended. Furthermore, the conditions under which the PCR reaction was conducted electrochemical in WO92/00470 differ from those of the conventional PCR process in that it was not found possible to use a conventional PCR buffer system. In order to obtain denaturation, it was necessary to conduct the process at a much lower ionic strength than would be consistent with such a buffer system. Excluding the promoter methyl viologen, the process was basically conducted in distilled water.

It has now been discovered that it is now possible to conduct a denaturation electrochemically considerably faster than is disclosed in WO92/04470 and to conduct an amplification procedure much faster than is disclosed there.

Although the spacing between the two working electrodes in WO92/04470 is not explicitly stated, it was in fact several millimetres.

Accordingly, the present invention provides a process for denaturing double-stranded nucleic acid which comprises subjecting a solution containing said nucleic acid to a voltage applied between electrodes under conditions such as to convert at least a portion of said nucleic acid to a wholly or partially single-stranded form in the solution, wherein said electrodes approach to within 1.5 mm of one another in said solution. Preferably, the electrodes approach more closely, e.g. within 1 mm or more preferably 0.5 mm of one another. Ideally, the electrodes are adjusted to be spaced by as little as possible whilst ensuring that they do not contact one another to produce a short circuit.

It is preferred to apply a voltage difference of from 0.5 to 3 volts between the electrodes. Voltage differences above 3 volts seem to inhibit denaturation although the mechanism involved here is presently unknown.

Preferably, the process is conducted at a voltage of 1.5 to 2.5 volts measured as a voltage difference between the electrodes.

Preferably, where the electrodes most closely approach one another, one or both of the electrodes is pointed. Such an electrode may be provided with a single point or a plurality of points. There appears to be some interrelationship between the ideal voltage applied and the shape of the electrode and it may be that there is a preferred or ideal field gradient at the point of the electrode which can be achieved by adjustment of the voltage to suit the sharpness of the part of the electrode at which the denaturation takes place. Optionally, one can conduct the denaturation using a constant current supply rather than a regulated voltage and this may serve to compensate for variations in the geometrical set-up of the electrodes between different denaturation operations.

Where a constant current regime is employed, it will generally be preferable to use a current of from 80 to 160 $\mu$A, e.g. about 100 to 125 $\mu$A.

As described in WO92/04470, one may employ a promoter compound such as methyl viologen to produce more rapid denaturation. Other promoters are described in WO93/15224, i.e. multivalent cations such as magnesium. Other multivalent cations which are effective and which can be used include lanthanum ($La^{3+}$). The cations used as the promoters may include inorganic cations complexed with inorganic or organic ligands, e.g. $Pt(NH_3)_6^{4+}$ and $Cr(NH_3)_6^{2+}$.

The promoter may be any inorganic or organic molecule which increases the rate of extent of denaturation of the double helix. It should be soluble in the chosen reaction medium. It preferably does not affect or interfere with DNA or other materials such as enzymes or oligonucleotide probes which may be present in the solution. Alternatively, the promoter may be immobilised to or included in material from which the electrode is constructed.

The promoter may be a water-soluble compound of the bipyridyl series, especially a viologen such as methyl-viologen or a salt thereof. Whilst the mechanism of operation of such promoters is presently not known with certainty, it is believed that the positively charged viologen molecules interact between the negatively charged nucleic acid such as DNA and the negatively charged cathode to reduce electrostatic repulsion therebetween and hence to promote the approach of the DNA to the electrode surface where the electrical field is at its strongest. Accordingly, we prefer to employ as promoters compounds having spaced positively charged centres, e.g. bipolar positively charged compounds. Preferably the spacing between the positively charged centres is similar to that in viologens. Other suitable viologens include ethyl-viologen, isopropyl viologen and benzyl viologen.

Optionally, the process may be conducted using a three electrode system of the kind described in WO92/04470 but generally it is preferred that the volume of solution employed according to this invention is small e.g. 1 ml or less, preferably very small e.g. 100 $\mu$l or less, e.g about 25 $\mu$l to 40 $\mu$l. When using very small reaction volumes of this kind, it will generally not be practical to use a three electrode system.

The process may be carried out at ambient temperatures or if desired at temperatures up to adjacent the pre-melting temperature of the nucleic acid. The process may be carried out at a pH of from 3 to 10, conveniently about 7. Generally, more rapid denaturation is obtained at lower pH. For some purposes therefore a pH somewhat below neutral e.g. about pH 5.5 may be preferred. The nucleic acid may be dissolved in an aqueous solution containing a buffer whose nature and ionic strength are such as not to interfere with the strand separation process.

Preferably, the solution contains a buffer at a concentration at least 10 mM, e.g. about 25 mM. Optionally, the solution may contain further salts such as magnesium chloride and sodium chloride. Preferably, the reaction is conducted in a buffer of the kind used in PCR or in LCR procedures.

Preferably therefore the ionic strength of the solution is above 20 mM, e.g. 25 to 50 mM.

The denaturing process according to the invention may be incorporated as a step in a number of more complex processes, e.g. procedures involving the analysis and/or the amplification of nucleic acid. Some examples of such processes are described below.

We have found that by virtue of the superior cell design described above, it is possible to achieve denatur-ation much more quickly than according to the teachings of WO92/04470 and even in the presence of materials such as PCR buffers which would prevent denaturation or extend denaturation times unreasonably in the apparatus described in WO92/04470. Making use of this shortened time, it is now possible to practice a process of denaturation which is brought to a conclusion within less than 3 minutes e.g. from 1 to 2 minutes or less.

This makes it possible to practice a process of repeated denaturation of double-stranded nucleic acid wherein the nucleic acid is denatured by a process as described above in which the voltage is applied as sequence of repeated pulses having a duration of up to 2 minutes, preferably up to only 1 minute. Between pulses, the voltage may be turned off or reversed for a period which is preferably equal to the period for which the voltage is applied. It is possible to employ pulses of considerably higher frequencies than described above, e.g. from 1 to 100 Hz. Depending upon the purpose for which the denaturation is being conducted, it may not be necessary to achieve any substantial amount of conversion of double-stranded to single-stranded nucleic acid in each denaturation cycle. It may be sufficiently merely to initiate denaturation electro-chemically. For instance, in an amplification procedure, if sufficient denaturation occurs to allow binding of a primer, the extension of the primer by nuclease may be relied upon to displace the unprimed strand of the original nucleic acid from its binding partner over the remainder of the length of the nucleic acid.

Taking advantage of the increased rate of denaturation now obtainable, the invention provides a process of amplifying a target sequence of nucleic acid comprising hybridisation, amplification and denaturation of nucleic acid wherein said denaturation is conducted by subjecting a solution containing said nucleic acid to a voltage applied between electrodes for a period of up to 2 minutes under conditions such as to convert at least a portion of the nucleic acid to a wholly or partially single-stranded form in the solution. Preferably, the electrode configuration used in such a process is as described above. Preferably, the voltage is applied as a repeating pulse having a duration of up to 2 minutes but preferably shorter, e.g. up to 1 minute or even much shorter, e.g. at 1 to 100 Hz.

Preferably, the amplification procedure is PCR or LCR.

Thus the present invention includes a process for replicating a nucleic acid which comprises: separating the strands of a sample double-stranded nucleic acid in solution under the influence of an electrical voltage applied to the solution form an electrode: hybridising the separated strands of the nucleic acid with at least one oligonucleotide primer that hybridises with at least one of the strands of the denatured nucleic acid; synthesising an extension product of the or each primer which is sufficiently complementary to the respective strand of the nucleic acid to hybridise therewith; and separating the or each extension product from the nucleic acid strand with which it is hybridised to obtain the extension product.

In such a polymerase mediated replication procedure, e.g. a polymerase chain reaction procedure, it may not be necessary in all cases to carry out denaturation to the point of producing wholly single-stranded molecules of nucleic acid. It may be sufficient to produce a sufficient local and/or temporary weakening or separation of the double helix in the primer hybridisation site to allow the primer to bind to its target. Once the primer is in position on a first of the target strands, rehybridisation of the target strands in the primer region will be prevented and the other target strand may be progressively displaced by extension of the primer or by further temporary weakening or separation processes.

Preferably, the said amplification process further comprises repeating the procedure defined above cyclicly, e.g. for more than 10 cycles, e.g. up to 20 or 30 cycles. In the amplification process the hybridisation step is preferably carried out using two primers which are complementary to different strands of the nucleic acid.

The denaturation to obtain the extension products as well as the original denaturing of the target nucleic acid is preferably carried out by applying to the solution of the nucleic acid the voltage from the electrodes.

The process may be a standard or classical PCR process for amplifying at least one specific nucleic acid sequence contained in a nucleic acid or a mixture of nucleic acids wherein each nucleic acid consists of two separate complementary strands, of equal or unequal length, which process comprises:

(a) treating the strands with two oligonucleotide primers, for each different specific sequence being applied, under conditions such that for each different sequence being amplified an extension product of each primer is synthesised which is complementary to each nucleic acid strand, wherein said primers are selected so as to be substantially complementary to different strands of each specific sequence such that the extension product synthesised from one primer, when it is separated from its complement, can serve as a template for synthesis of the extension product of the other primer;

(b) separating the primer extension products from the templates on which they were synthesised to produce single-stranded molecules by applying the voltage from the electrode to the reaction mixture; and (c) treating the single-stranded molecules generated from step (b) with the primers of step (a) under conditions such that a primer extension product is synthesised using each of the single strands produced in step (b) as a template.

Alternatively, the process may be any variant of the classical or standard PCR process, e.g. the so-called "inverted" or "inverse" PCR process or the "anchored" PCR process.

The invention therefore includes an amplification process as described above in which a primer is hybridised to a circular nucleic acid and is extended to form a duplex which is denatured by the denaturing process of the invention, the amplification process optionally being repeated through one or more additional cycles.

The process of the invention is applicable to the ligase chain reaction. Accordingly, the invention includes a process for amplifying a target nucleic acid comprising the steps of:

(a) providing nucleic acid of a sample as single-stranded nucleic acid;

(b) providing in the sample at least four nucleic acid probes, wherein:
  i) the first and second said probes are primary probes, and the third and fourth of said probes are secondary nucleic acid probes;
  ii) the first probe is a single strand capable of hybridising to a first segment of a primary strand of the target nucleic acid;
  iii) the second probe is a single strand capable of hybridising to a second segment of said primary strand of the target nucleic acid;
  iv) the 5' end of the first segment of said primary strand of the target is positioned relative to the 3' end of the second segment of said primary strand of the target to enable joining of the 3' end of the first probe to the 5' end of the second probe, when said probes are hybridised to said primary strand of said target nucleic acid;
  v) the third probe is capable of hybridising to the first probe; and
  iv) the fourth probe is capable of hybridising to the second probe; and (c) repeatedly or continuously:
  i) hybridising said probes with nucleic acid in said sample;
  ii) ligating hybridised probes to form reorganised fused probe sequences; and
  iii) denaturing DNA in said sample by applying a voltage from an electrode configuration as described to the reaction mixture.

The electrochemical DNA amplification technique can be used analytically to detect and analyse a very small sample of DNA e.g a single copy gene in an animal cell or a single cell of a bacterium.

The temperature at which the process is carried out may be chosen to suit whichever enzyme is used. Thus where Taq is used as polymerase, a temperature of 55 to 68° C. is preferred. If Klenow polymerase is used, ambient temperature will be suitable. It may be desirable to employ known protein stabilisation techniques to avoid electrical damage to the polymerase, especially where a mesophilic polymerase is used.

The invention includes a process for detecting the presence or absence of a predetermined nucleic acid sequence in a sample which comprises: denaturing a sample double-stranded nucleic acid by means of a voltage applied to the sample in a solution by means of electrodes spaced as described above; hybridising the denatured nucleic acid with an oligonucleotide probe for the sequence; and determining whether the said hybridisation has occurred.

Thus, the invented process has application in DNA and RNA hybridisation where a specific gene sequence is to be identified e.g. specific to a particular organism or specific to a particular hereditary disease of which sickle cell anaemia is an example. To detect a specific sequence it is first necessary to prepare a sample of DNA, preferably of purified DNA, means for which are known, which is in native double-stranded form. It is then necessary to convert the double-stranded DNA to single-stranded form before a hybridisation step with a labelled nucleotide probe which has a complementary sequence to the DNA sample can take place. The denaturation process of the invention can be used for this purpose in a preferred manner by carrying out the following steps:

denaturing a sample of DNA by applying a voltage by means of an electrode configuration as described to the sample DNA with optionally a promoter in solution or bound to or part of the structure of the electrode;

hybridising the denatured DNA with a directly labelled is or indirectly labelled nucleotide probe complementary to the sequence of interest; and determining whether the hybridisation has occurred, which determination may be by detecting the presence of the probe, the probe being directly radio-labelled, fluorescent labelled, chemiluminescent labelled or enzyme-labelled or being an indirectly labelled probe which carries biotin for example to which a labelled avidin or avidin type molecule can be bound later.

In a typical DNA probe assay it is customary to immobilise the sample DNA to a membrane surface which may be composed of neutral or charged nylon or nitrocellulose. The immobilisation is achieved by charge interactions or by baking the membrane containing DNA in an oven. The sample DNA can be heated to high temperature to ensure conversion to single-stranded form before binding to the membrane or it can be treated with alkali once on the membrane to ensure conversion to the single-stranded form. The disadvantages of such methods are:

heating to high temperature to create single-stranded DNA can cause damage to the.sample DNA itself.

the use of alkali requires an additional step of neutralisation before hybridisation with the labelled probe can take place.

One improved method for carrying out DNA probe hybridisation assays is the so-called "sandwich" technique where a specific oligonucleotide is immobilised on a surface. The surface having the specific oligonucleotide thereon is then hybridised with a solution containing the target DNA in a single-stranded form, after which a second labelled oligonucleotide is then added which also hybridises to the target DNA. The surface is then washed to remove unbound labelled oligonucleotide, after which any label which has become bound to target DNA on the surface can be detected later.

This procedure can be simplified by using the denaturing process of the invention to denature the double-stranded DNA into the required single-stranded DNA. The working electrode, counter-electrode and optionally a reference electrode and/or a promoter can be incorporated into a test surface or a well in which the DNA probe assay is to be carried out. The DNA sample and oligonucleotide probes can then be added and the voltage applied to denature the DNA. The resulting single-stranded DNA is hybridised with the specific oligonucleotide immobilised on the surface after which the remaining stages of a sandwich assay are carried out. All the above steps can take place without a need for high temperatures or addition of alkali reagents as in the conventional process.

The invention includes an electrochemical cell for use in the denaturation of nucleic acid comprising a well having an electrically conductive inner surface constituting a first electrode, and a second electrode dipping into said well and reaching to close proximity to the floor of said well. Preferably, the well is formed in a body of conductive material constituting the second electrode. Both the well and the second electrode may be of conductive carbon such as graphite.

The invention further includes a kit for use in a nucleic acid assay or amplification comprising an electro-chemical cell of this kind and at least one of a nucleic acid for denaturation, an oligonucleic acid, one or more nucleotides, a polymerase, a ligase and/or a buffer solution.

The invention will be further described and illustrated with reference to the accompanying drawing which is a cross-sectional view through a cell for use in accordance with the invention.

The cell illustrated comprises a graphite block 10, containing a 4 mm diameter well 12 on its upper surface, constituting a first electrode. A second electrode formed from a 2 mm diameter graphite rod 14 having a tapering end portion 16 is pressed into the well through an insulating collar of plastics material 18. The rod is adjusted downwards in the well until it forms a short circuit and is then lifted back by as little as possible to open the circuit again. The capacity for liquid for the cell is approximately 25 $\mu$l. A DC voltage is applied to the apparatus with the well being made positive with respect to the rod by preferably 1.6 to 2.4 volts.

Although the rod electrode shown in FIG. 1 is blunt ended, it provides a sharp edge between its flat end and its tapering frustoconical surface. An optional alternative configuration is for the rod to be sharpened to a point. This may be achieved by using a conventional pencil sharpener. The resulting electrode may be further smoothed using a blade or abrasive. Using such a pointed electrode, the capacity for liquid of the well is increased to 40 $\mu$l.

Multiple processes according to the invention may be carried out simultaneously in apparatus containing a multiplicity of sample receiving wells each provided with a respective electrode pair, one electrode in each case optionally being the well itself. In a preferred form for such apparatus a block containing the wells has a liftable lid with electrodes depending therefrom into the wells. Each well may have a pair of electrodes on the lid in various possible electrode conformations such as parallel rods, parallel plates, optionally of mesh, or coaxial hollow cylinders, again optionally of mesh. Alternatively, single electrodes may be provided on the lid for each well and the block containing the wells may be conductive and may serve as a common second electrode. The block of wells may also contain respective electrodes for each well.

The lid may comprise a flat plate portion bearing the electrode or electrodes for each well and a separate backing member bearing electrical connections and circuitry which connects up the electrodes when the two parts are assembled. A single electrical supply to the unit may be split by said circuitry and supplied in a controlled manner to the electrodes such that each electrode is controlled, e.g. to a constant voltage or constant current. The plate portion carrying the electrode array may thereby be replaceable without replacement of the control circuitry and may be made disposable. The plate portion and the backing member may be aligned with one another on assembly by locating pins and apertures and may similarly by aligned with the block containing the wells, which also may be disposable.

The following examples illustrate the use of the apparatus described above and methods according to the invention in comparison to techniques described in WO92/04470.

Example 1

Denaturation of DNA was carried out in the cell shown in FIG. 1, modified by the use of a pointed electrode 14, using a constant voltage of 2.4 V. Denaturation of 40 $\mu$l of calf thymus DNA (12 $\mu$g/ml) in 1 mM methyl viologen was completed in 1 to 2 minutes.

Comparative Example 1

Using the three electrode electrical system described in WO92/04470, DNA was denatured using -IV at the working electrode with respect to the calomel reference electrode (~2.4V). Denaturation of 1 ml of calf thymus DNA (4 $\mu$g/ml) in 1 mM methyl viologen was completed in about 25 minutes.

Example 2

Denaturation of calf thymus DNA was carried out using a constant voltage of 2.4 V between the electrode of the cell of FIG. 1, modified by the use of a pointed electrode 14. Denaturation of 40 $\mu$l DNA (20 $\mu$g/ml) in 25 mM KPO$_4$, pH 6.0, 1 mM methyl viologen was completed in 1 to 2 minutes.

Comparative Example 2

Using the three electrodes of WO92/04470 DNA was denatured using -IV at the working electrode with respect to the calomel reference electrode (~2.4V). Denaturation of 1 ml calf thymus DNA (4 $\mu$g/ml) in 25 mM Tris, pH 7.5, 1 mM methyl viologen, required more than 180 minutes.

Whilst the invention has been described above in terms of the preferred embodiments illustrated by the examples, many modifications and variations thereof are possible within the scope of the invention.

I claim:

1. A process for denaturing double-stranded nucleic acid which comprises subjecting a solution containing said nucleic acid to a voltage applied between electrodes under conditions such as to convert at least a portion of said nucleic acid to a wholly or partially single stranded form in the solution, wherein said electrodes approach to within 1.5 mm of one another in said solution.

2. A process as claimed in claim 1, wherein the electrodes approach to within 1 mm of one another in said solution.

3. A process as claimed in claim 1, wherein the electrodes approach to within 0.5 mm of one another in said solution.

4. A process as claimed in claim 1, wherein a voltage of from 0.5 to 3 volts is applied between said electrodes.

5. A process as claimed in claim 4, wherein a voltage of from 1.5 to 2.5 volts is applied between said electrodes.

6. A process as claimed in claim 1, wherein the solution contains a promoter which assists said denaturation.

7. A process as claimed in claim 6, wherein said promoter is methyl viologen or a salt thereof, or is a multivalent inorganic cation.

8. A process as claimed in claim 7, wherein said promoter is magnesium or lanthanum ions.

9. A process as claimed in claim 1, wherein where the electrodes most closely approach one another, one or both of the electrodes is pointed.

10. A process of repeated denaturation of double-stranded nucleic acid, wherein the nucleic acid is denatured by a process for denaturing double-stranded nucleic acid which comprises subjecting a solution containing said nucleic acid to a voltage applied between electrodes under conditions such as to convert at least a portion of said nucleic acid to a wholly or partially single stranded form in the solution, wherein said electrodes approach to within 1.5 mm of one another in said solution, and in which said voltage is applied as a repeating pulse having a duration of up to 2 minutes.

11. A process of repeated denaturation as claimed in claim 10, wherein said voltage is applied as a repeating pulse having a duration of up to 1 minute.

12. A process of repeated denaturation as claimed in claim 10, wherein between said pulses the voltage is turned off or reversed for a period equal to the period for which the voltage is applied.

13. A process of repeated denaturation as claimed in claim 12, wherein said voltage is applied as pulses at a frequency of from 1 to 100 Hz.

14. A process of amplifying a target sequence of nucleic acid comprising hybridisation, amplification and denaturation of nucleic acid wherein said denaturation is conducted by subjecting a solution containing said nucleic acid to a voltage applied between electrodes for a period of up to 2 minutes under conditions such as to convert at least a portion of said nucleic acid to a wholly or partially single stranded form in the solution.

15. A process of amplifying a target sequence of nucleic acid as claimed in claim 14, wherein said electrodes approach to within 1.5 mm of one another in said solution.

16. A process of amplifying a target sequence of nucleic acid as claimed in claim 14, wherein said voltage is applied as a repeating pulse having a duration of up to 2 minutes.

17. A process of amplifying a target sequence of nucleic acid as claimed in claim 14, wherein said voltage is applied as a repeating pulse having a duration of up to 1 minute.

18. A process of amplifying a target sequence as claimed in claim 14, which is a PCR or LCR amplification.

19. An electrochemical cell for use in the denaturation of nucleic acid comprising a well having an electrically conductive inner surface constituting a first electrode and a second electrode dipping into said well and reaching to within 1.5 mm of the floor of said well.

20. A kit for use in a nucleic acid assay or amplification, comprising an electrochemical cell as claimed in claim 19, and at least one of:

a nucleic acid for denaturation;

an oligo-nucleic acid;

one or more nucleotides;

a polymerase;

a ligase; and a buffer solution.

21. An electrochemical cell for use in the denaturation of nucleic acid comprising a well having a floor with an electrically conductive inner surface which constitutes a first electrode, and a second electrode separate from the well which dips into the well and reaches to within proximity of the floor of the well.

22. The electrochemical cell of claim 21, wherein the second electrode is adjustable in height with respect to the floor of the well so as to reach to close proximity to the floor of the well.

23. An electrochemical cell for use in the denaturation of nucleic acid comprising a plurality of wells, each said well having an electrically conductive inner surface constituting an electrode, said plurality of wells forming a first array of electrodes, and a second array of electrodes separate from said first array of electrodes, wherein at least one electrode of said second array of electrodes dips into at least one well of said plurality of wells so as to reach to close proximity to the electrically conductive inner surface of said at least one well.

* * * * *